United States Patent
Gurtner et al.

(10) Patent No.: US 9,636,362 B2
(45) Date of Patent: May 2, 2017

(54) PULLULAN REGENERATIVE MATRIX

(75) Inventors: Geoffrey C. Gurtner, Palo Alto, CA (US); Kirit Bhatt, Evans, GA (US); Jayakumar Rajadas, Cupertino, CA (US)

(73) Assignee: The Board of Trustees of The Leland Stanford Junior University, Palo Alto, CA (US)

( * ) Notice: Subject to any disclaimer, the term of this patent is extended or adjusted under 35 U.S.C. 154(b) by 472 days.

(21) Appl. No.: 12/932,736

(22) Filed: Mar. 3, 2011

(65) Prior Publication Data

US 2011/0305745 A1    Dec. 15, 2011

Related U.S. Application Data

(60) Provisional application No. 61/339,559, filed on Mar. 4, 2010.

(51) Int. Cl.

| | | |
|---|---|---|
| *A61K 38/39* | (2006.01) | |
| *A61K 8/73* | (2006.01) | |
| *A61K 35/28* | (2015.01) | |
| *A61L 15/22* | (2006.01) | |
| *A61L 15/40* | (2006.01) | |
| *A61L 15/42* | (2006.01) | |
| *A61L 15/44* | (2006.01) | |
| *A61L 15/60* | (2006.01) | |
| *A61L 27/26* | (2006.01) | |
| *A61L 27/38* | (2006.01) | |
| *A61L 27/48* | (2006.01) | |
| *A61L 27/52* | (2006.01) | |
| *A61L 27/54* | (2006.01) | |
| *A61L 27/56* | (2006.01) | |
| *A61K 9/70* | (2006.01) | |

(52) U.S. Cl.
CPC ............. *A61K 35/28* (2013.01); *A61K 8/732* (2013.01); *A61K 38/39* (2013.01); *A61L 15/225* (2013.01); *A61L 15/40* (2013.01); *A61L 15/425* (2013.01); *A61L 15/44* (2013.01); *A61L 15/60* (2013.01); *A61L 27/26* (2013.01); *A61L 27/3804* (2013.01); *A61L 27/48* (2013.01); *A61L 27/52* (2013.01); *A61L 27/54* (2013.01); *A61L 27/56* (2013.01); *A61K 9/7007* (2013.01); *A61L 2300/404* (2013.01); *A61L 2300/414* (2013.01)

(58) Field of Classification Search
CPC .................................................... A61K 35/28
See application file for complete search history.

(56) References Cited

U.S. PATENT DOCUMENTS 4,841,962 A *  6/1989  Berg et al. ...................... 602/50
2010/0221301 A1*  9/2010  Le Visage et al. ........... 424/422

FOREIGN PATENT DOCUMENTS

WO    WO-2007124023 A2 *  11/2007  ............... C21N 5/08

OTHER PUBLICATIONS

Abed; et al., "A Biocompatible Polysaccharide Hydrogel—Embedded Polypropylene Mesh for Enhanced Tissue Integration in Rats", Tissue Engineering: Part A (2008), 14(4):519-527.
Autissier; et al., "Pullulan-based hydrogel for smooth muscle cell culture", Journal of Biomedical Materials Research Part A (2007), 82(2):336-342.
Badiavas; et al., "Participation of Bone Marrow Derived Cells in Cutaneous Wound Healing", Journal of Cellular Physiology, Journal of Cellular Physiology (2003), 196:245-250.
Kataoka; et al., "Participation of Adult Mouse Bone Marrow Cells in Reconstitution of Skin", American Journal of Pathology (2003), 163(4):1227-1231.
Kato; et al., "Nanogel-Based Delivery System Enhances PGE2 Effects on Bone Formation", Journal of Cellular Biochemistry (2007), 101:1063-1070.
Lataillade; et al., "New approach to radiation burn treatment by dosimetry-guided surgery combined with autogous mesechymal stem cell therapy", Regen. Med. (2007), 2(5):785-794.
Shimizu; et al., "Nanogel DDS enables sustained release of IL-12 for tumor immunotherapy", Biochemical and Biophysical Research Communications (2008), 367(2):330-5.
Thebaud; et al., "Human endothelial progenitor cell attachment to polysaccharide-based hydrogels: a pre-requisite for vascular tissue engineering", J Mater Sci: Mater Med (2007), 18(2):339-345.
Wu; et al., "Mesenchymal Stem Cells Enhance Wound Healing Through Differentiation and Angiogenesis", Stem Cells (2007), 25(10): 2648-59.

* cited by examiner

*Primary Examiner* — Abigail Fisher
*Assistant Examiner* — Jessica Kassa
(74) *Attorney, Agent, or Firm* — Levine Bagade Han LLP

(57) ABSTRACT

Compositions and methods are provided for the manufacture and use of a pullulan-based collagen hydrogel film with controlled porosity. The hydrogel is fabricated with salt-induced phase inversion and cross-linking to form a reticular scaffold. This soft collagen scaffold displays excellent handling characteristics, durability, and a porous dermal-like ultrastructure that is maintained in vitro. Cells, including cells involved in tissue repair, are viably sustained within the scaffold. The hydrogel films are biodegradable, and find particular use in wound healing, where the hydrogel scaffold can be replaced by dermal cells over time.

22 Claims, 12 Drawing Sheets

Polarizing Light Polarizing Light w/
 Picrosirius Red

PULLULAN REGENERATIVE MATRIX

FEDERALLY SPONSORED RESEARCH AND DEVELOPMENT

This invention was made with Government support under contract W81XWH-08-2-0032 awarded by the U.S. Army Medical Research Acquisition Activity. The Government has certain rights in this invention.

BACKGROUND

Scars form in response to cutaneous injury as part of the natural wound healing process. Wound healing is a lengthy and continuous process, although it is typically recognized as occurring in stages. The process begins immediately after injury, with an inflammatory stage. During this stage, which typically lasts from two days to one week (depending on the wound), damaged tissues and foreign matter are removed from the wound. The proliferative stage occurs at a time after the inflammatory stage and is characterized by fibroblast proliferation and collagen and proteoglycan production. It is during the proliferative stage that the extracellular matrix is synthesized in order to provide structural integrity to the wound. The proliferative stage usually lasts about four days to several weeks, depending on the nature of the wound, and it is during this stage when hypertrophic scars usually form. The last stage is called the remodeling stage. During the remodeling stage the previously constructed and randomly organized matrix is remodeled into an organized structure that is highly cross-linked and aligned to increase mechanical strength.

The ability to repair the human body without scarring has been a goal of the medicine for many years. Human tissue banks and synthetic polymers are not currently meeting the need for repair or replacement of body parts, and thus there is a large market for advanced tissue engineering products, both synthetic and biologicals. However, tissue engineered skin substitutes provide only limited success in replacing skin. Synthetic polymers, plastics, and surface-coated metals may have different degrees of immunogenicity and suffer from significant limitations that prohibit their broad applications. A major limitation is that cells cannot remodel them after implantation. They are highly susceptible to microbial infection, and some undergo calcification. Furthermore, synthetic vascular conduits have a high incidence of occlusion after peripheral vascular bypass procedures.

Tissue engineering of skin requires biomaterial techniques capable of recapitulating both cellular and non-cellular elements. An important non-cellular element that plays a critical role in regulating skin behavior is the dermal extracellular matrix (ECM). This complex environment not only houses the myriad cell types involved in skin homeostasis and repair, but also provides mechanical stability, enables metabolite and cellular movement, and is constantly remodeled in response to local and systemic cues. Dermal scaffolds, derived from both native and synthetic sources, constitute the foundation for skin replacement techniques and have been used with variable success. Native dermal sources, such as decellularized cadaveric skin, are limited by cost, donor availability, and disease transmission concerns.

Current skin substitutes comprise of primitive animal collagen scaffolds that provide a conduit for tissue ingrowth. The success of these scaffolds has been limited due to poor incorporation by the host tissue, resulting in the formation of scar tissue rather than regenerated skin. In addition to poor tissue ingrowth, these products are plagued by infection, chronic inflammation, allergic reaction, excessive redness, pain, swelling, or blistering. Therefore, there is an urgent need for more complex skin substitutes that are nontoxic, biodegradable, and closely resemble a regenerative environment.

Improved skin substitutes for preventing or ameliorating the formation of scars and improving healing are therefore desirable for many clinical purposes.

PUBLICATIONS

Abed et al. (2008) Tissue Eng Part A. 14 (4):519-27 describes a biocompatible polysaccharide hydrogel-embedded polypropylene mesh for enhanced tissue integration in rats. A cholesterol-bearing pullulan (CHP)-based hydrogel nanoparticles, or nanogel was used to encapsulate interleukin-12 by Shimizu et al. (2008) Biochem Biophys Res Commun. 367 (2):330-5; or to deliver prostaglandin E2 (Kato et al. (2007) J Cell Biochem. 101 (5):1063-70.

Thébaud et al. (2007) J Mater Sci Mater Med. 18 (2):339-45 prepared a hydrogel from polysaccharides (pullulan/dextran/fucoidan) and evaluated as a biomaterial for endothelial progenitor cell (EPC) culture. Autissier et al. (2007) J Biomed Mater Res A. 82 (2):336-42 utilized hydrogel from pullulan as a biomaterial for vascular engineering after seeding with vascular smooth muscle cells.

Wu et al. (2007) Stem Cells 25 (10):2648-59 describe mesenchymal stem cells enhance wound healing through differentiation and angiogenesis. Kataoka et al. (2003) Am J Pathol. 163 (4):1227-31 disclose participation of adult mouse bone marrow cells in reconstitution of skin. Badiavas et al. (2003) J Cell Physiol. 196 (2):245-50 discuss participation of bone marrow derived cells in cutaneous wound healing. Lataillade et al. (2007) Regen Med. 2 (5):785-94 teach an approach to radiation burn treatment by dosimetry-guided surgery combined with autologous mesenchymal stem cell therapy.

SUMMARY

Compositions and methods are provided for the manufacture and use of a pullulan-based collagen hydrogel film with controlled porosity. The hydrogel is fabricated with salt-induced phase inversion and cross-linking to form a reticular scaffold. This soft collagen scaffold displays excellent handling characteristics, durability, and a porous dermal-like ultrastructure that is maintained in vitro. Cells, including cells involved in tissue repair, are viably sustained within the scaffold. The hydrogel films are biodegradable, and find particular use in wound healing, where the hydrogel scaffold can be replaced by dermal cells over time.

In some embodiments of the invention, a hydrogel composition is provided, which hydrogel comprises pullulan; and collagen at a concentration of from about 1% to about 10% of the total dry weight, and may be around about 5% of the total dry weight. The hydrogel comprises pores of controlled size, usually pores of from about 10-100 µm in diameter. In some embodiments the hydrogel comprises cells within the scaffold. Alternatively, or in addition, the hydrogel may comprise protein ligands, e.g. protein ligands involved in cell growth, including, without limitation, growth factors, chemokines, cytokines, fibronectin, cell adhesive peptides (RGDS), laminin, and the like.

In some embodiments of the invention the hydrogel provides a scaffold for cell growth, including growth of regenerative cells. The cells may be grown in vitro, e.g. the culture of cells, including regenerative cells such as stem cells, lineage committed progenitors, etc. The cells will usually be contact oriented cells. Cells may also be grown in vivo, e.g. where a hydrogel film provides a substrate for regenerative cell growth, e.g. as a wound covering or artificial skin construct.

In some embodiments of the invention methods are provided for the fabrication of porous collagen scaffolds within a pullulan-based hydrogel system. In the fabrication methods, a salt-induced phase invention method is used to create the porous films of the invention. The porosity provides an ultrastructure that readily accommodates cell growth.

In one embodiment of the invention a system is provided for cell growth, comprising at least one hydrogel film as a substrate for cell growth. The film is optionally sterile. The system may further comprise a vessel suitable for cell growth, e.g. a flask, multi-well plate, etc., where the hydrogel film is present within the vessel. The system may further comprise a dressing suitable for wound repair, e.g. an inner surface of a hydrogel thin film, and an outer surface structure that protects the wound, e.g. a protective outer layer.

In another embodiment of the invention, methods are provided for regenerative growth of tissues in vivo, the method comprising contacting a tissue surface, e.g. a dermal surface, with a hydrogel film, for a period of time sufficient to allow cell migration to, and growth on, the hydrogel. Such a hydrogel optionally comprises cell growth factors, chemokines, etc. to enhance the regenerative growth.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF THE SPECIFIC EMBODIMENTS

Figure 1:
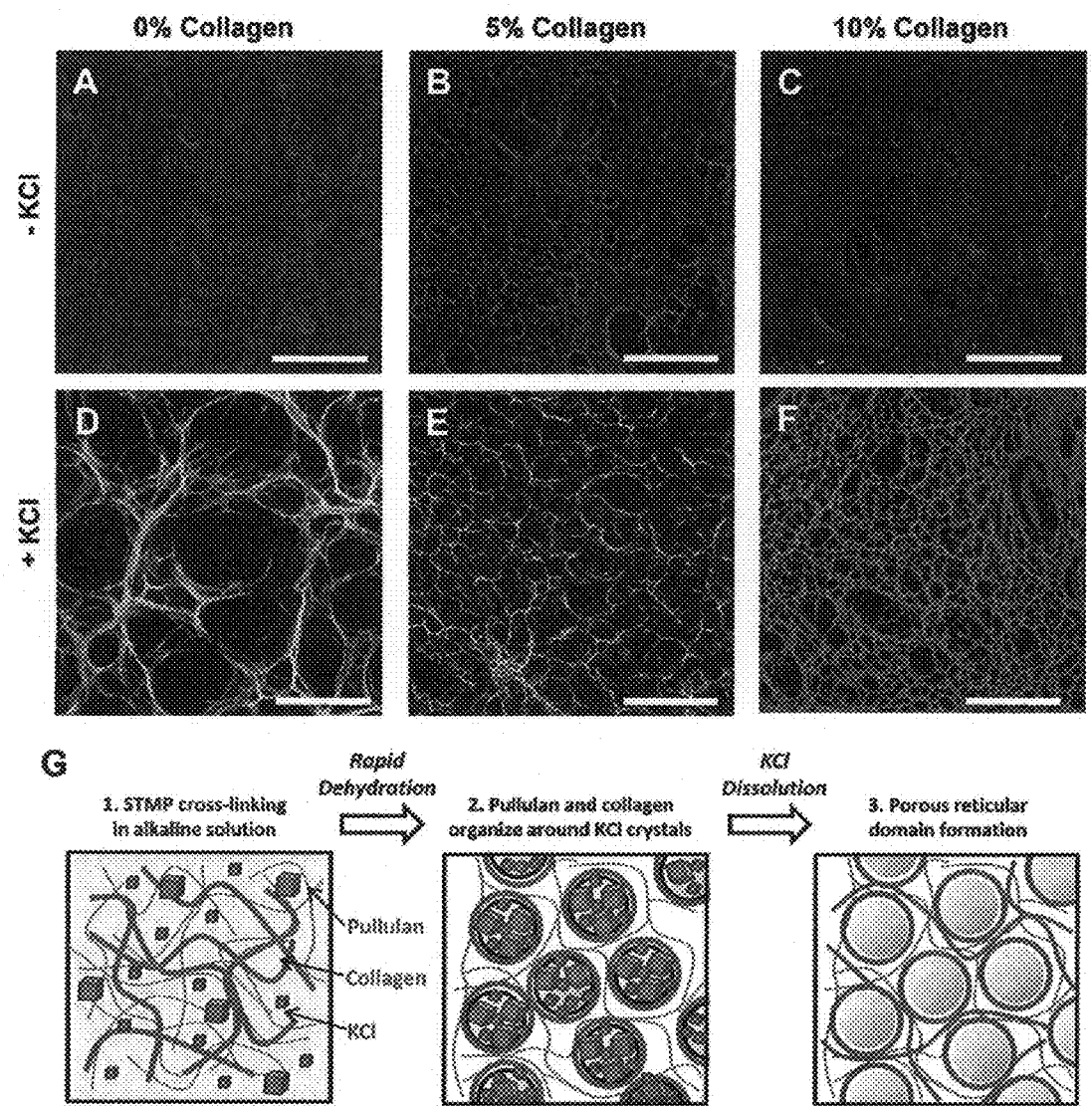
FIGS. 1A-1G: Hydrogel porous properties at different collagen concentrations. SEM imaging revealed that pullulan hydrogels fabricated without KCl demonstrated poor porosity, despite increases in collagen content (A-C). With the addition of KCl however, regular porous domains were created (D-F). We hypothesize that KCl crystallization induces pore formation through phase inversion (G). As water is rapidly removed from the hydrogel, localized supersaturation of KCl results in crystallization around which polymers become organized. As dissolution occurs, KCl is washed out from the hydrogel, leaving porous voids around which pullulan+/− collagen are organized, in the process forming a reticular scaffold. Scale bar is 100 microns.

Compositions and methods are provided for cell growth, including growth of regenerative cells, on a hydrogel film. The cells may be grown in vitro or in vivo. The hydrogel film is fabricated with salt-induced phase inversion and cross-linking to form a reticular scaffold. This soft scaffold displays excellent handling characteristics, durability, and a porous dermal-like ultrastructure. Scaffold characteristics of interest include pore microarchitecture, swelling ratio, viscoelasticity, degradation, and cross-linking properties, which variables may be designed to fall within specific parameters.

Dermal micro-architecture plays a pivotal role in directing cells towards a regenerative pathway. For example, when a defect is made in early gestation fetal skin, cells regenerate the defect readily. The microfabricated and patterned hygroscopic biomimetic matrices of the present invention recreate the dermal architecture of embryonic skin. This architecture promotes the initiation of a regenerative healing response.

In addition to architecture, the composition of the fetal skin and wound matrix comprises unique protein ligands and stem cells. The pullulan matrices of the invention recapitulate the fetal environment by mimicking the fetal architecture, fetal protein structure, and maintaining stem cells.

Pullulan hydrogels are cross-linked order to control degradation rate, incorporate stem cells, including without limitation patient-specific stem cells. The hydrogels may further comprise protein ligands mimicking the fetal wound healing environment. Protein ligands are printed on the pullulan hydrogels by precise micro-contact printing methods. With the addition of stem cells and proprietary fetal-ligand patterning on the matrices, the matrices function as intelligent, biodegradable, regenerative skin substitutes.

Pullulan hydrogel matrices comprising stem cells and ligands promote scar-free tissue regeneration. The combination of stem cells, protein ligands, and antimicrobials make these hydrogels an intelligent version of current FDA approved biologic dressings (i.e., Integra, Alloderm, Apligraf). The dressings are suitable for burn patients, diabetic ulcers, venous ulcers, partial- and full-thickness wounds, pressure ulcers, chronic vascular ulcers, trauma wounds, draining wounds, and surgical wounds. The regenerative dressing is easily be applied in the first few hours following injury and debridement, and can remain in place until regeneration occurs.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Hydrogel Film.

Carbohydrate-based hydrogels were fabricated using pullulan and collagen under conditions that provided for cross-linking and pore formation. Collagen is added to a mixture of pullulan, cross-linking agent and pore forming agent (porogen), where the collagen is provided at a concentration of at least about 1%, and not more than about 12.5% relative to the weight of the pullulan. Collagen may be provided at a concentration of about 1%, about 2.5%, about 5%, about 7.5%, about 10%, usually at a concentration of from about 2.5% to about 10%, and may be from about 4% to about 6%, which collagen is typically a fibrous collagen, e.g. Type I, II, III, etc. Cross-linking agents of interest include sodium trimetaphosphate (STMP) or a combination of or a combination of sodium trimetaphosphate and sodium tripolyphosphate (STMP/STPP). Porogens of interest for in-gel crystallization include any suitable salt, e.g. KCl.

The composition is poured and compressed to form sheets. Preferred thickness is at least about 1 mm and not more than about 5 mm, usually not more than about 3 mm, and may be from about 1.75 to 2.5 mm, e.g. about 2 mm thick.

Pores are formed in the hydrogel through rapid desiccation of swollen hydrogels by phase inversion. Dehydration results in localized supersaturation and crystallization of the porogen. Pullulan and collagen are forced to organize around the crystals in an interconnected network which results in reticular scaffold formation following KCl dissolution. This is the first demonstration of porogen crystallization-induced pore formation applied to fabricate collagen scaffold hydrogels. The addition of a porogen augments hydrogel viscoelasticity. The improved scaffold porosity allows for greater fluid absorption, a higher water to polymer ratio, and more effective hydrogel behavior.

The films may be stored in a dried state, and are readily rehydrated in any suitable aqueous medium. The aqueous nature of hydrogel substrates provides an ideal environment for cellular growth and sustainability. The collagen scaffold hydrogels showed high biocompatibility with fibroblasts, ASCs, and endothelial cells. In addition, fibroblasts and ASCs were well incorporated into these scaffolding constructs. These data demonstrate that collagen scaffold hydrogel delivery of wound repair and progenitor cells can be used following dermal injury.

This soft collagen scaffold displays excellent handling characteristics, durability, and a porous dermal-like ultrastructure that is maintained in vitro. Furthermore, cell types potentially involved in skin repair are viable sustained within these biomatrices. This biocompatible collagen scaffold promises to broaden hydrogel applications for skin engineering and can potentially be used to deliver organized matrix components, cells, and biomolecules for skin regeneration.

Mechanical features of the hydrogel include average pore size and scaffold porosity. Both variables vary with the concentration of collagen that is present in the hydrogel. For a hydrogel comprising 5% collagen, the average pore size will usually range from about 25 µm to about 50 µm, from about 30 µm to about 40 µm, and may be about 35 µm. For a hydrogel comprising 10% collagen the average pore size will usually range from about 10 µm to about 25 µm, from about 12 µm to about 18 µm, and may be about 15 µm. One of skill in the art will readily determine suitable hydrogels at other collagen concentrations. The scaffold porosity will usually range from about 50% to about 85%, and may range from about 70% to about 75%, and will decrease with increasing concentrations of collagen.

Hydrogels lacking collagen do not display any birefringence with polarizing light microscopy, while the hydrogels comprising collagen are diffusely birefringent.

Pullulan.

A polysaccharide produced by the fungus *Aureobasidium pullulans*. It is a linear homopolysaccharide consisting of alpha-(1-6) linked maltotriose units and exhibits water retention capabilities in a hydrogel state which makes it an ideal therapeutic vehicle for both cells and biomolecules. Additionally, pullulan contains multiple functional groups that permit crosslinking and delivery of genetic material and therapeutic cytokines. Furthermore, pullulan-based scaffolds have been shown to enhance both endothelial cell and smooth muscle cell behavior in vitro.

Collagen.

As used herein the term "collagen" refers to compositions in which at least about 50%, at least about 60%, at least about 70%, at least about 80%, at least about 90%, at least about 95% or more of the protein present is collagen in a triple helical configuration. Collagens are widely found in vertebrate species, and have been sequenced for many different species. Due to the high degree of sequence similarity between species, collagen from different species can be used for biomedical purposes, e.g. between mammalian species. Typical commercial animal sources include the bovine Achilles tendon, calfskin and the bones of cattle. In some embodiments the collagen used in the preparation of the oriented thin film is Type I, Type II or Type III collagen, and is derived from any convenient source, e.g. bovine, porcine, etc., usually a mammalian source.

Collagen has a triple-stranded ropelike coiled structure. The major collagen of skin, tendon, and bone is collagen I, containing 2 alpha-1 polypeptide chains and 1 alpha-2 chain. The collagen of cartilage contains only 1 type of polypeptide chain, alpha-1. The fetus also contains collagen of distinctive structure. The genes for types I, II, and III collagens, the interstitial collagens, exhibit an unusual and characteristic structure of a large number of relatively small exons (54 and 108 bp) at evolutionarily conserved positions along the length of the triple helical gly-X-Y portion.

Types of collagen include I (COL1A1, COL1A2); II (COL2A1); III (COL3A1); IV (COL4A1, COL4A2, COL4A3, COL4A4, COL4A5, COL4A6); V (COL5A1, COL5A2, COL5A3); VI (COL6A1, COL6A2, COL6A3); VII (COL7A1); VIII (COL8A1, COL8A2); IX (COL9A1, COL9A2, COL9A3); X (COL10A1); XI (COL11A1, COL11A2); XII (COL12A1); XIII (COL13A1); XIV (COL14A1); XV (COL15A1); XVI (COL16A1); XVII (COL17A1); XVIII (COL18A1); XIX (COL19A1); XX (COL20A1); XXI (COL21A1); XXII (COL22A1); XXIII (COL23A1); XXIV (COL24A1); XXV (COL25A1); XXVII (COL27A1); XXVIII (COL28A1). It will be understood by one of skill in the art that other collagens, including mammalian collagens, e.g. bovine, porcine, equine, etc. collagen, are equally suitable for the methods of the invention.

Supports.

A variety of solid supports or substrates may be used with the hydrogel, including deformable. By deformable is meant that the support is capable of being damaged by contact with a rigid instrument. Examples of deformable solid supports include polyacrylamide, nylon, nitrocellulose, polypropylene, polyester films, such as polyethylene terephthalate; PDMS (polydimethylsiloxane); etc. as known in the art for the fabrication of wound dressings.

Cells.

The hydrogel films of the invention provide a substrate for cell growth, which may be vertebrate cells, e.g. mammalian cells, where the term refers to any animal classified as a mammal, including humans, domestic and farm animals, and zoo, laboratory, sports, or pet animals, such as dogs, horses, cats, cows, mice, rats, rabbits, etc. Preferably, the mammal is human. The cells which are employed may be fresh, frozen, or have been subject to prior culture. They may be fetal, neonate, adult. The cells may be primary cell cultures, cell lines, cells present in an animal, etc.

Preferably the cells are regenerative, that is they give rise to new cells and tissues, e.g. as stem cells, progenitor cells, lineage committed progenitor cells, and the like. Fibroblasts and other epithelial precursor cells may also be included. The term stem cell is used herein to refer to a cell that has the ability both to self-renew, and to generate differentiated progeny (see Morrison et al. (1997) Cell 88:287-298). Generally, stem cells also have one or more of the following properties: an ability to undergo asynchronous, or symmetric replication, that is where the two daughter cells after division can have different phenotypes; extensive self-renewal capacity; capacity for existence in a mitotically quiescent form; and clonal regeneration of all the tissue in which they exist, for example the ability of hematopoietic stem cells to reconstitute all hematopoietic lineages. "Progenitor cells" differ from stem cells in that they typically do not have the extensive self-renewal capacity, and often can only regenerate a subset of the lineages in the tissue from which they derive, for example only lymphoid, or erythroid lineages in a hematopoietic setting.

Stem cells may be embryonic or fetal stem cells, which can be pluripotent, totipotent, or lineage committed. Pluripotent stem cells are cells derived from any kind of tissue (usually embryonic tissue such as fetal or pre-fetal tissue), which stem cells have the characteristic of being capable under appropriate conditions of producing progeny of different cell types that are derivatives of all of the 3 germinal layers (endoderm, mesoderm, and ectoderm). These cell types may be provided in the form of an established cell line, or they may be obtained directly from primary embryonic tissue and used immediately for differentiation. Included are cells listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)).

Stem cells of interest also include embryonic cells of various types, exemplified by human embryonic stem (hES) cells, described by Thomson et al. (1998) Science 282:1145; embryonic stem cells from other primates, such as Rhesus stem cells (Thomson et al. (1995) Proc. Natl. Acad. Sci USA 92:7844); marmoset stem cells (Thomson et al. (1996) Biol. Reprod. 55:254); and human embryonic germ (hEG) cells (Shamblott et al., Proc. Natl. Acad. Sci. USA 95:13726, 1998). Also of interest are lineage committed stem cells, such as mesodermal stem cells and other early cardiogenic cells (see Reyes et al. (2001) Blood 98:2615-2625; Eisenberg & Bader (1996) Circ Res. 78 (2):205-16; etc.) The stem cells may be obtained from any mammalian species, e.g. human, equine, bovine, porcine, canine, feline, rodent, e.g. mice, rats, hamster, primate, etc.

Stem cells of interest also include adult stem cells, which include mesodermal stem and progenitor cells, neural crest stem and progenitor cells, liver stem and progenitor cells, pancreatic stem and progenitor cells, mesenchymal stem and progenitor cells, epidermal skin and progenitor cells, etc.

Cells may be initially seeded or grown for one to two days grown on the hydrogel thin film in vitro, where the thin film is placed in a suitable vessel for culture, e.g. a flask, plate, multiwell plate, etc. The cells are grown in vitro in an appropriate liquid nutrient medium. Generally, the seeding level will be at least about 10 cells/ml, more usually at least about 100 cells/ml and generally not more than about $10^5$ cells/ml, usually not more than about $10^4$ cells/ml. Any cell culture medium appropriate for growth and differentiation of cells may be used in cell cultures employing the present collagen cell culture substrates. These include, but are not limited to, DMEM, MEM, M-199 and RPMI. Supplements, as are known in the art, may be added to the culture medium and include serum (e.g., FBS or calf serum), serum-containing supplements (N IU-SERUM), and serum-free supplements (MITO+).

Regenerative Factors.

Polypeptide growth factors and cell-signalling molecules may be included in the hydrogel. Protein ligands are printed on the pullulan hydrogels by precise micro-contact printing methods. Alternatively the proteins may be included in the initial fabrication of the matrix. Polypeptides of interest as growth factors include, without limitation, the following molecules, where one or more of the factors may be patterned on a matrix. The native form of the polypeptides may be used, or variants thereof, e.g. truncated versions that maintain biological activity; stabilized variants; conjugated engineered for improved adhesion to the hydrogel matrix, and the like.

Platelet-derived growth factor (PDGF) is a family of potent activators for cells of mesenchymal origin, and a stimulator of chemotaxis, proliferation and new gene expression in monocytes, macrophages and fibroblasts, accelerating ECM deposition. This family of growth factors exists in both homo- and heterodimeric forms.

Cytokines of the transforming growth factor-β family (TGF-β) are multifunctional regulators of cell growth, differentiation and ECM formation. In mammals, there are three isoforms, TGF-β1, TGF-β2 and TGF-β3. In particular, in relation to wound healing in the skin, TGF-β1 and TGF-β2 are implicated in cutaneous scarring, whereas TGF-β3 is known to have an anti-scarring effect.

Bone morphogenetic proteins (BMPs) are members of the TGF-β superfamily. There are 15 members and although they are known for their role in bone and cartilage formation, they have diverse roles in many other developmental processes.

Fibroblast growth factors (FGFs) are a family of 21 isoforms with a broad spectrum of activities, including regulation of cell proliferation, differentiation and migration. FGFs 1, 2, 5, 7 and 10 are upregulated during adult cutaneous wound healing. bFGF may have the ability to accelerate tissue regeneration in artificial dermis.

Vascular endothelial growth factor (VEGF) is induced during the initial phase of skin grafting, where endogenous fibrin clots are known to form a provisional matrix and to promote angiogenesis. Growth factors such as VEGF increase in such wounds to stimulate angiogenesis.

Epidermal growth factor (EGF) has been implicated in wound healing and homeostasis in a number of tissues.

Hepatocyte growth factor/scatter factor (HGF/SF) is a pleiotrophic growth factor produced principally by cells of mesenchymal origin. HGF has been implicated in enhancing the cutaneous wound healing processes of re-epithelialization, neovascularization and granulation tissue formation.

Antimicrobial Agents.

The hydrogels may further comprise antimicrobial agents. Agents of interest include a wide variety of antibiotics, as known in the art. Classes of antibiotics include penicillins, e.g. penicillin G, penicillin V, methicillin, oxacillin, carbenicillin, nafcillin, ampicillin, etc.; penicillins in combination with β lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical, metronidazole; spectinomycin; trimethoprim; vancomycin; etc. Antiviral agents, e.g. acyclovir, gancyclovir, etc. may also be included.

Wound Dressing.

Hydrogel films of the invention find use as a wound dressing, or artificial skin, by providing an improved substrate that minimizes scarring. An effective bioactive wound dressing can facilitate the repair of wounds that may require restoration of both the epidermis and dermis. An hydrogel thin film is placed onto, and accepted by, the debrided wound of the recipient and provide a means for the permanent re-establishment of the dermal and epidermal components of skin. The graft suppresses the formation of granulation tissue which causes scarring.

Additional criteria for biologically active wound dressings include: rapid adherence to the wound soon after placement; proper vapor transmission to control evaporative fluid loss from the wound and to avoid the collection of exudate between the wound and the dressing material. Skin substitutes should act as barrier to microorganisms, limit the growth of microorganisms already present in the wound, be flexible; durable and resistant to tearing. The substitute should exhibit tissue compatibility, that is, it should not provoke inflammation or foreign body reaction in the wound which may lead to the formation of granulation tissue. An inner surface structure of an hydrogel thin film is provided that permits ingrowth of fibro-vascular tissue. An outer surface structure may be provided to minimize fluid transmission and promote epithelialization.

Typical bioabsorbable materials for use in the fabrication of porous wound dressings, skin substitutes and the like, include synthetic bioabsorbable polymers such as polylactic acid or polyglycolic acid, and also, biopolymers such as the structural proteins and polysaccharides. The finished dressing prior to cell seeding is packaged and preferably radiation sterilized. Such biologically active products can be used in many different applications that require the regeneration of dermal tissues, including the repair of injured skin and difficult-to-heal wounds, such as burn wounds, venous stasis ulcers, diabetic ulcers, etc.

Devices and Methods

Devices are described here for ameliorating the formation of scars and/or keloids at a wound site. The scars may be any type of scar, e.g., a normal scar, a hypertrophic scar, etc. In general, the devices are configured to be removably secured to a skin surface near a wound. The devices of the invention comprise a porous, cross-linked collagen-pullulan hydrogel matrix, which comprises regenerative cells. The regenerative cells may be epithelial cells, endothelial cells, fibroblasts, stem cells, and the like. Usually the hydrogel will be seeded with cells prior to use, e.g. by culturing cells in the hydrogel for about 3 to about 24 hours. The hydrogel may further comprise regenerative protein factors, as described herein, which protein factors may be specifically patterned on the hydrogel, or may be integrated in the matrix, or otherwise coupled to the hydrogel scaffold. A diverse array of active agents or ingredients may be present in the hydrogel patch compositions, as described above. Depending on the nature of the agent, the amount of active agent present in the composition may ranges from about 0.2 to 10%, e.g., from about 0.2 to 5%, e.g., from about 0.5 to 5%. The pH of the hydrogel patch compositions typically is one that lies in a physiologically acceptable range, where the pH typically ranges from about 3.0 to 8.0 and more typically ranges from about 4.0 to 7.0.

The hydrogel would dressing may be attached or adhered to a substrate, e.g. a breathable protective layer, or other protective film. Alternatively the hydrogel dressing may be separately configured from a protective dressing. In certain embodiments, a hydrogel dressing composition may be present on a support or backing. The support is generally made of a flexible material which is capable of fitting in the movement of the human body and includes, for example, various non-woven fabrics, woven fabrics, spandex, flannel, or a laminate of these materials with polyethylene film, polyethylene glycol terephthalate film, polyvinyl chloride film, ethylene-vinyl acetate copolymer film, polyurethane film, and the like. By "flexible" it is meant that the support may be substantially bent or folded without breaking, tearing, ripping, etc. The support may be porous or non-porous, but is typically non-porous or impermeable to the hydrogel composition, active agent if employed and fluids, e.g., any fluids exuded from the wound site.

The length and width dimensions of the support are typically substantially commensurate, including exactly or commensurate, with the length and width dimensions of the hydrogel patch composition with which it is associated. The support layer typically may have a thickness that ranges from about 10 µm to about 1000 µm, but may be less than about 10 µm and/or greater than 1000 µm in certain embodiments.

In addition to the hydrogel patch composition and the optional support layer, the subject patches may also include a release film on the surface of the hydrogel composition layer opposite the backing that provides for protection of the hydrogel composition layer from the environment. The release film may be any convenient material, where representative release films include polyesters, such as PET or PP, and the like.

The shape of the dressing may vary, where representative shapes include square, rectangle, oval, circle, triangular, etc. The size of the dressing may also vary, where in many embodiments the size ranges from about 1 cm$^2$ or less to about 1000 cm$^2$ or more, e.g., in certain embodiments ranges from about 10 to about 300 cm$^2$, e.g., from about 20 to about 200 cm$^2$, e.g., about 130 cm$^2$ to about 150 cm$^2$. In certain embodiments, the surface area is sufficient to cover a substantial portion or even the entire truck or even a substantial portion of the entire body or even the entire body of a subject. Accordingly, the surface area may range from about 1000 cm$^2$ to about 5000 cm$^2$ or more. It should be noted that the above manufacturing protocol is merely representative. Any convenient protocol that is capable of producing the subject hydrogel patch compositions, as described above, may be employed.

The subject methods find use in any application in which the treatment of a wound of a subject is desired. Generally, such subjects are "mammals" or "mammalian", where these terms are used broadly to describe organisms which are within the class mammalia, including the order carnivore (e.g., dogs and cats), rodentia (e.g., mice, guinea pigs, and rats), and primates (e.g., humans, chimpanzees, and monkeys). In many embodiments, the subject is a human.

Accordingly, the subject methods may be used to treat a wide variety of open- and closed-skin wounds such that the subject methods may be used to treat wounds that have resulted from a variety of causes, e.g., as a result of a condition such as a disease state, a physical injury such as a fall, scrape, stab wound, gun shot, surgical wound, infection, etc., wartime injuries such as bombs, bullets, shrapnel. Likewise, the subject methods may treat wounds of various dimensions. For example, the subject methods may be employed to with both deep tissue wounds and shallow or superficial wounds, where certain wounds may have depths that reach the muscle. Wounds may be confined to the epidermis such that they do not penetrate into the dermal layer, may be as deep as the dermis or deeper, e.g., may penetrate to or through the dermis and even to or through the subcutaneous tissue layer or deeper, e.g., may penetrate through or to the muscle layer or further. For example, the subject methods may be used to debride wounds that having a depth that ranges from about 0.005 mm to about 2.35 mm, e.g., from about 0.007 mm to about 2.3 mm, e.g., from about 0.01 mm to about 2 mm.

Types of wounds that may be treated with the subject invention include, but are not limited to, ulcers, including pressure ulcers, diabetic ulcers (e.g., diabetic foot ulcers), venous ulcers, lower leg ulcer, etc.; burns (first, second and third degree burns) including scalds, chemical burns, thermal burns such as flame burns and flash burns, ultraviolet burns, contact burns, radiation burns, electrical burns, etc.; bone infections (osteomyelitis); gangrene; skin tears or lacerations, such as made by knives, etc.; abrasions; punctures such as made by nails, needles, wire, and bullets, etc.; incisions such as made by knives, nails, sharp glass, razors, etc.; avuls; amputations; post-operative infections; surgical wounds; brown recluse spider wounds; failing or compromised skin/muscle grafts or flaps; bites; slash wounds, i.e., a wound where the length is greater than the depth; bruises; and the like, or a combination of one or more of the above.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

Such biologically active products can be used in many different applications that require the regeneration of dermal tissues, including the repair of injured skin and difficult-to-heal wounds, such as burn wounds, venous stasis ulcers, diabetic ulcers, etc.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXPERIMENTAL

Example 1

Materials and Methods:

Materials and animals. Carbohydrate-based hydrogels were fabricated using pullulan ($M_w$ 200,000, Hayashibara Laboratories, Okayama, Japan). Collagen was prepared from rat tail collagen type 1 solution (Sigma-Aldrich, St. Louis, Mo.). Cross-linking was performed with sodium trimetaphosphate (STMP, Sigma-Aldrich) under alkaline conditions with sodium hydroxide (Sigma-Aldrich). Potassium chloride salt (KCl, Sigma-Aldrich) was used as a porogen for in-gel crystallization. 100% ethyl alcohol (Sigma-Aldrich) was used for hydrogel dehydration. Pullulanase (Sigma-Aldrich) was prepared in a concentration of 4 U/mL in phosphate buffered saline (PBS) (Gibco, Grand Island, N.Y.). Collagenase A (Roche, Indianapolis, Ind.) was prepared in a concentration of 2 mg/mL in PBS. Methylene blue (Sigma-Aldrich) was used to quantify STMP cross-linking per previously published methods. All aqueous solutions were prepared in deionized water. All compounds and reagents were used without further purification.

Murine adipose-derived mesenchymal stem cells (ASCs) were harvested as previously published. Fibroblasts were obtained from a primary line of human foreskin fibroblasts, passage 3. bEnd.3 endothelial cells were obtained from American Type Culture Collection (Manassas, Va.). Cells were maintained in Dulbecco's Modified Eagle's Medium (DMEM) (4.5 g/mL glucose, Gibco) supplemented with 10% fetal bovine serum (v/v) and 1% penicillin/streptomycin.

10-12 week old male wild type C57BL/6 (Jackson Laboratories, Bar Harbor, Me.) were used for normal skin and ASC harvest. Mice were fed ad libitum water and rodent chow and housed in the Stanford University animal facility under institution-approved guidelines.

Hydrogel Fabrication.

Based on previously published methods, 2 g of pullulan was mixed with 2 g of STMP and 2 g KCl in 50 mg NaOH dissolved in 10 mL of deionized $H_2O$. Collagen was then added at a concentration of 0, 5, or 10% of the weight of pullulan. The composite mixture was mechanically stirred for 30 minutes at 4° C. The mixture was then poured onto Teflon sheets and compressed to create 2 mm thick films. Hydrogel films were then dehydrated in 100% ethyl alcohol for 15 minutes and allowed to dry overnight. Dried films were then washed in PBS at room temperature until the wash pH was 7.0 and stored at 4° C. until further use. 6 mm punch biopsy disks of 2 mm thickness were used for all experiments. Films were sterilized overnight under UV light in a cell culture hood prior to experiments.

Scanning Electron Microscopy (SEM).

Air-dried hydrogel samples were mounted onto adhesive carbon film on 15 mm aluminum stubs, and sputter-coated with 100 Å gold/palladium using a Denton Desk II TSC Sputter Coater (Denton Vacuum, Moorestown, N.J.). Visualization was carried out with a Hitachi S-3400N VP SEM (Hitachi Ltd, Pleasanton, Calif.) operated at 10-15 kV with a working distance 8-10 mm and secondary electron detection. Hydrated hydrogels were mounted onto 10 mm stubs fitting a Deben Peltier cool stage (Deben, Suffolk, England) set at 4° C. inside the specimen chamber of a Hitachi S-3400N VP-SEM. The Variable Pressure SEM allows observation of non-conductive samples in their natural state, eliminating the need for sample preparation. To limit water loss, pressure and temperature were correlatively decreased until a chamber pressure of 60 Pa and correlated stage temperature of −25° C. were reached. Backscattered electron (BSE) detection was used to capture images at 15 kV, at a working distance of 8-10 mm.

For in vitro cellular incorporation studies, fibroblasts and ASCs were seeded onto 5% collagen-pullulan hydrogels in cell culture media for 72 hours. Scaffold/cell samples were fixed for 24 hours at 4° C. with 4% paraformaldehye and 2% glutaraldehyde in 1N sodium cacodylate buffer pH 7.3 (Electron Microscopy Sciences, Hatfield, Pa.). Fixed samples were washed in the same buffer, and post-fixed for one hour in 1% aqueous osmium tetroxide, washed in deionized water, and visualized with BSE as described above. At least ten random SEM fields were examined at low magnification to assess consistency of porosity. Pore size was calculated from ten random pores from ten high power SEM fields using ImageJ software (National Institutes of Health, Bethesda, Md.). Porosity was measured from ten high power SEM fields for each condition using the threshold function and area measurement tool in ImageJ.

Network Extraction Analysis.

Reference images from unwounded adult murine skin were obtained from confocal imaging of picrosirius red stained tissue sections using previously published methods. Briefly, 0.5 μm sections along the entire 8 μm section were stacked and merged into 1024 by 1024 pixel images using a Leica SP2 AOBS confocal microscope (Leica Microsystems, Wetzlar, Germany) equipped with a 543 nm helium-neon green laser.

Polarizing Light Microscopy.

Hydrogels were visualized under polarizing microscopy to assess collagen orientation and fiber characteristics, with organized collagen fibrils displaying birefringence. Hydrogel samples stained with Picrosirius red were qualitatively analyzed for collagen fibril size, since large fibrils emit yellow/red and small fibrils emit green. Two sets of 0% and 5% collagen-pullulan films were allowed to incubate in PBS at room temperature, and one set was subsequently stained with picrosirius red for 15 minutes. Hydrogel films were then viewed under polarizing microscopy at 200× magnification (Leica DM 5000B).

Swelling Property.

The amount of hydrogel swelling correlates with the degree of crosslinking and is calculated as a swelling ratio (grams liquid/grams protein):

Swelling Ratio=(Weight of wet sample−Weight of dry sample)/Weight of dry sample

5% collagen-pullulan hydrogels were incubated in deionized water or in PBS overnight at 4° C. or 37° C. Excess liquid was gently shaken off and weights of swollen gels were obtained. Three samples were tested for each condition.

Rheologic Testing.

Dynamic rheometer, Angular frequency, Experiments performed at room temperature. Oscillatory stress. Strain, Time.

Frequency sweep testing was performed at 23° C. Strain sweep testing was performed at 23° C.

Degradation Rate.

Dry 5% collagen-pullulan hydrogels were incubated with pullulanase (4 U/mL) in PBS and weights were taken every 30 minutes. Similar experiments were performed with collagenase A (2 mg/mL in PBS). Doses were based on published methods. Combination degradation studies using both pullulanase and collagenase A were conducted in PBS using similar concentrations as above. Experiments were performed six times for each condition at room temperature.

Quantification of Cross-Linking.

Methylene blue absorption shows a linear relationship with STMP cross-linking density. Dried pullulan-based hydrogels containing 0% collagen with no STMP, 0% collagen with STMP, and 5% collagen with STMP were incubated overnight with methylene blue. Initial absorption of methylene blue pre-incubation was recorded at 665 nm ($A_0$) and again recorded after overnight incubation (A). Results were normalized with dry pre-incubation hydrogel weight (Wt) in milligrams. Four samples were tested for each condition. A methylene blue absorption index ($AI_{MB}$) was calculated based on modification of a previously published equation:

$$AI_{MB}=[(A_o-A)/Wt]\times 1000$$

Scaffold $AI_{MB}$ was calculated using:

$$\text{Scaffold } AI_{MB}=(AI_{MB} \text{ for 0\% collagen with no STMP})-(AI_{MB} \text{ for sample})$$

In Vitro Viability.

The ability of 5% collagen-pullulan hydrogel scaffolds to support cellular survival in vitro was assessed. Fibroblasts, ASCs, and endothelial cells were separately incubated with hydrogels for 72 hours. Cells were seeded at a density of $1\times 10^5$ cells per cm$^2$ in a 5% $CO_2$ incubator at 37° C. Cellular morphology was assessed daily and cellular survival was assessed with a live/dead assay (Calbiochem, Gibbstown, N.J.) per manufacturer instructions. Images were obtained with fluorescence microscopy (Zeiss Axioplan 2 Imaging, Carl Zeiss, Inc. Thornwood, N.Y., USA) with band-pass filters set to detect FITC and rhodamine. Identical high power field images obtained from different lasers were merged using Adobe Photoshop CS3 (Adobe Systems Incorporated, San Jose, Calif.) to create single images of red and green co-excitation. Live cells stained green while only dead cells stained red. Cell counts of at least 20 cells per high power field were taken from five random fields for each cell type.

Statistical Analysis.

SPSS17 software (SPSS Inc. Chicago, Ill.) was used to perform Student's t-test for univariate analysis. P value<0.05 was considered significant.

Results:

Mechanical Properties of Hydrogels.

Hydrogels were grossly durable, homogeneous, stable, and could be easily manipulated and handled. Dried hydrogel films were readily cut into consistent 6 mm disks of 2 mm thickness and incubation in aqueous solution resulted in a swollen, flexible, clear semi-rigid gel.

Porous Microarchitecture of Hydrogel Scaffolds.

Figure 2:
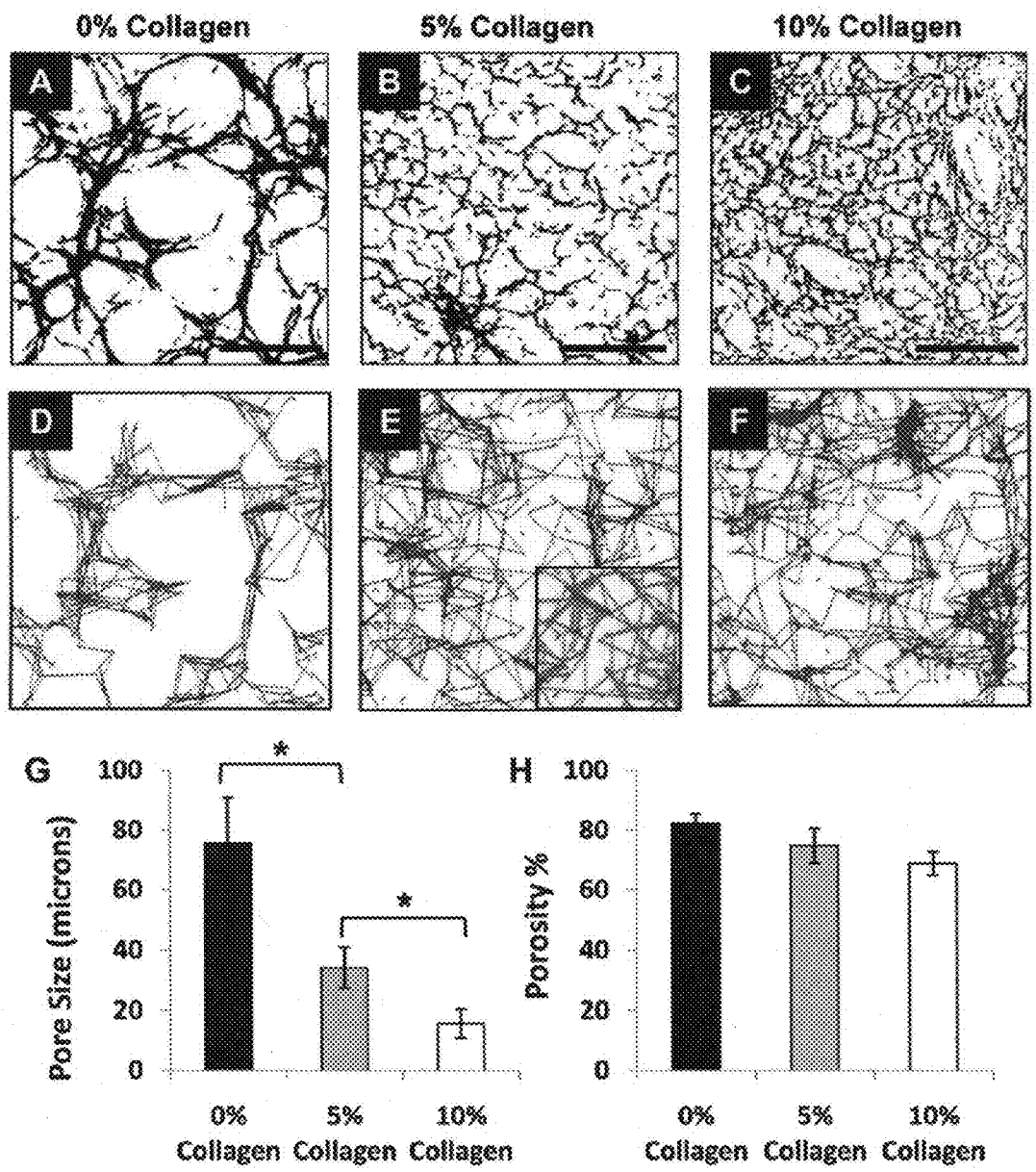
FIG. 2A-2H: A network extraction algorithm was used to analyze the microstructure of pullulan-based hydrogels (A-F). 5% collagen-pullulan hydrogel scaffolds best approximated the reticular collagen domains found in unwounded adult murine dermis (E, inset). 0% collagen scaffolds had an average pore size of 75 um±2.16, 5% collage-pullulan scaffolds contained an average pore size of 34.15 um±0.96, and 10% collagen-pullulan hydrogels had an average pore size of 15.70 um±0.67 (G, p<0.05). Scaffold porosity was determined using ImageJ threshold analysis and was approximately 82%, 75%, and 69% for hydrogels containing collagen at 0%, 5%, and 10% respectively (H).

Hydrogel porosity was induced by addition of KCl. Control pullulan+/− collagen hydrogels fabricated without KCl displayed minimal porosity (FIG. 1A-C) while the addition of KCl resulted in an interconnected, highly porous scaffold (FIG. 1D-F). Average pore sizes of 75 um±2.16, 34.15 um±0.96, and 15.70 um±0.67 (p<0.05) were calculated for 0%, 5%, and 10% collagen-pullulan hydrogels, respectively (FIG. 2G). Network extraction analysis found that hydrogel porous ultrastructure (FIG. 2A-F) approximated the dermal reticular collagen network of unwounded adult murine skin (FIG. 2E, inset). Scaffold porosity was approximately 82%, 75%, and 69% for hydrogels containing collagen at 0%, 5%, and 10% respectively (FIG. 2H).

Polarizing Light Studies.

Figure 3:
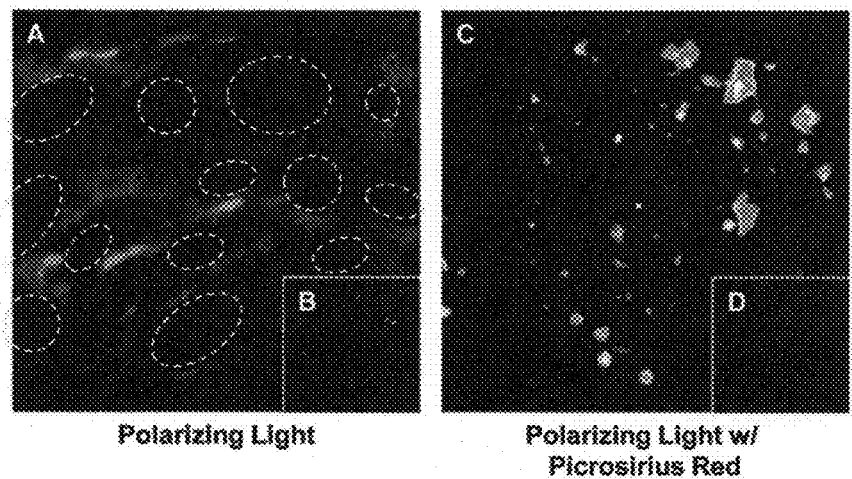
FIG. 3A-3D: Polarizing light evaluation. 5% collagen-pullulan hydrogels displayed positive birefringence on polarizing light (A) which was corroborated with Picrosirius red staining (B). Pullulan hydrogels with 0% collagen did not display any birefringence as expected (B and D). In conjunction with the SEM data, this suggests that organized collagen is diffusely arranged around pores (A, white dashed outline) and organized into different sized fibrils.

The above results demonstrated that pullulan hydrogels form porous domains without collagen (FIG. 1D). However, collagen interactions are important in matrix homeostasis so we investigated the distribution, orientation, and size of collagen domains within our hydrogel scaffolds. As expected, 0% collagen hydrogels did not display any birefringence with polarizing light microscopy (FIGS. 3B and 3D). 5% collagen hydrogels were diffusely birefringent (FIG. 3A) and this was corroborated by collagen-specific Picrosirius red staining (FIG. 3C), demonstrating well-spaced fibrils of various sizes.

Hydrogel Swelling.

Figure 4:
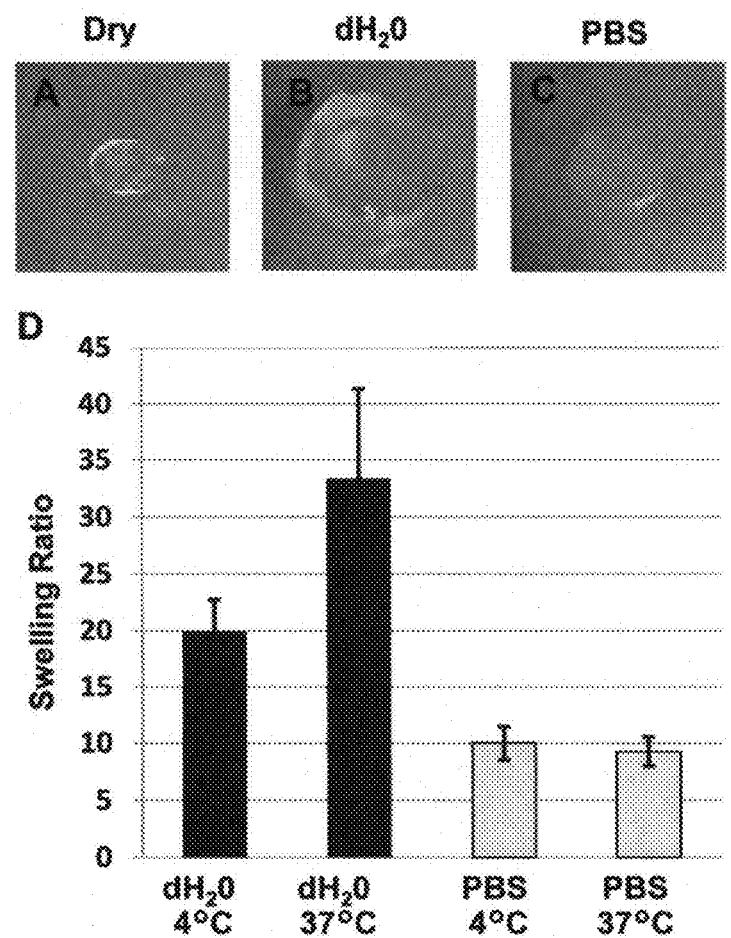
FIG. 4A-4D: 5% collagen-pullulan hydrogel hydration properties. Digital photographs of dry (A) and $dH_2O$- (B) and PBS-incubated (C) pullulan hydrogels following overnight incubation. Swelling ratios for 5% collagen-pullulan hydrogels were calculated following incubation in both $dH_2O$ and PBS (D). Incubation in $dH_2O$ resulted in a swelling ratio of 19.9±2.8 at 4° C. and 33.4±8.0 at 37° C. Incubation in PBS demonstrated a swelling ratio of 10.0±1.5 at 4° C. and 9.3±1.3 at 37° C. This demonstrates that 5% collagen-pullulan hydrogels are capable of effectively absorbing water while maintaining their structural integrity. N=6 for each condition.

Swollen hydrogels retained their general shape and were not degraded after overnight incubation in either deionized water or PBS (FIG. 4A-C). Swelling ratios for 5% collagen-pullulan hydrogels incubated in deionized water at 4° C. and 37° C. were 19.92±2.83 and 33.36±7.97, respectively (FIG. 4D). Swelling ratios for 5% collagen-pullulan hydrogels incubated in PBS at 4° C. and 37° C. were 9.99±1.47 and 9.27±1.29, respectively (FIG. 4D).

Rheologic Studies.

Figure 5:
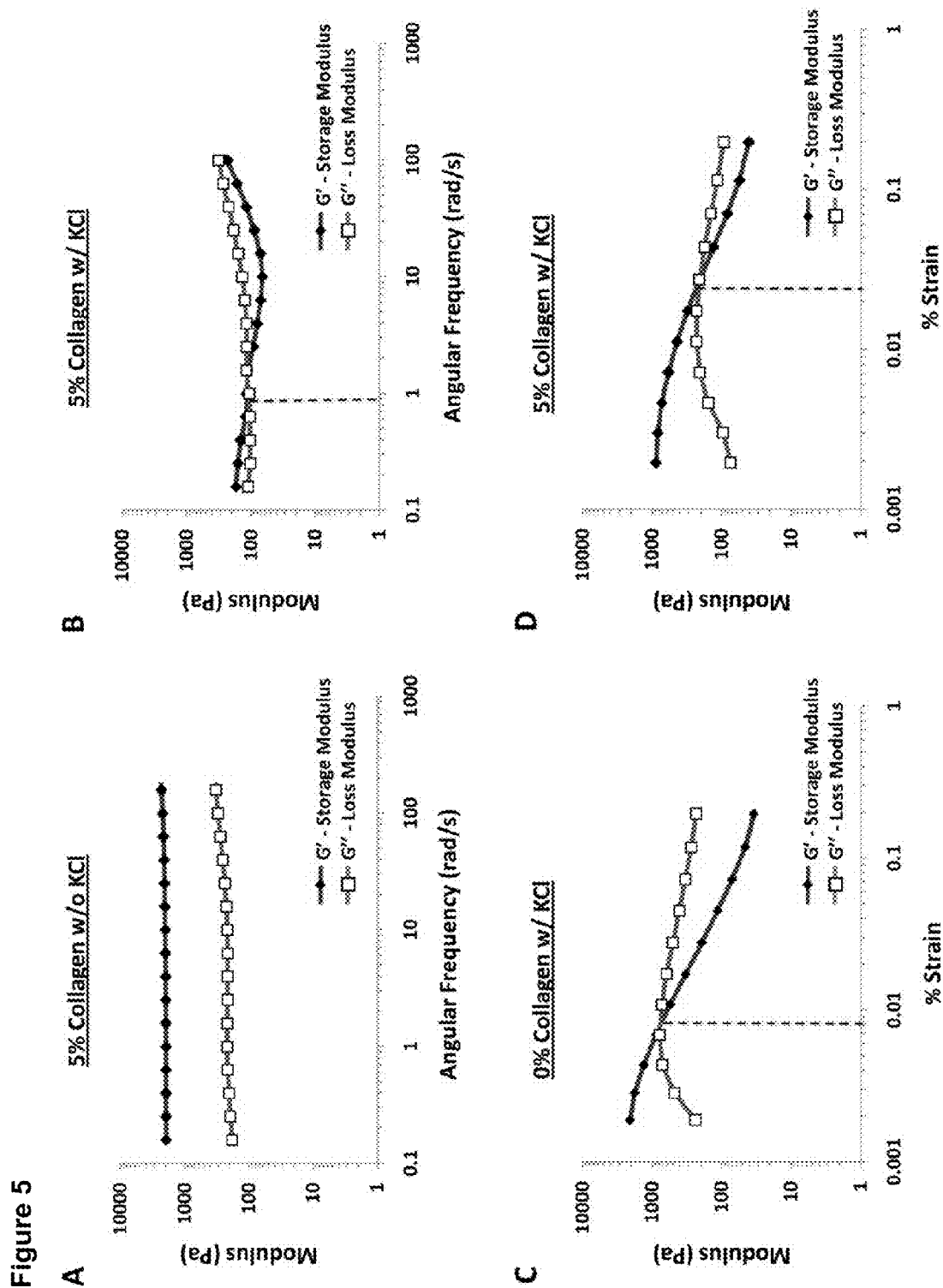
FIG. 5A-5D: Rheologic testing of 5% collagen-pullulan hydrogels. Based on frequency sweep testing, hydrogels without KCl demonstrate a several-fold higher storage modulus G' compared to loss modulus G", consistent with elastic solid-like behavior (A). However, when KCl is added, the hydrogel exhibits storage and loss moduli that are closely related and have a dynamic crossover point around 1 rad/s, both consistent with viscoelastic behavior (B). To assess the effect of collagen on hydrogel behavior, strain sweep testing was performed on hydrogels without (C) and with 5% collagen (D). The dynamic crossover point represents at what strain the hydrogel begins to break down (the loss modulus is then greater than the storage modulus). The addition of collagen increases the dynamic crossover point and demonstrates that the addition of collagen increases the strength of the hydrogels.

5% collagen-pullulan hydrogels with no KCl and 5% collagen-pullulan hydrogels with KCl were subjected to frequency sweep testing to characterize viscoelastic behavior under oscillatory shear stress. 5% collagen-pullulan hydrogels without KCl (FIG. 5A) exhibited a storage modulus several fold greater than loss modulus over the range of frequencies tested. These properties are characteristic of an elastic solid-like gel. However, with the addition of KCl, there is significant overlap of storage and loss moduli with a dynamic crossover point around 1 rad/second (FIG. 5B), characteristics of a viscoelastic hydrogel. To assess the effect of collagen on hydrogel behavior, strain sweep testing was performed on hydrogels with (FIG. 5D) and without collagen (FIG. 5C). The dynamic crossover point represents where increasing strain results in hydrogel breakdown (the loss modulus is greater than the storage modulus) and this was increased from approximately 0.008% strain to 0.015% strain with the addition of 5% collagen.

Hydrogel Degradation.

Incubation of 5% collagen-pullulan hydrogels with collagenase A (2 mg/mL) at room temperature resulted in scaffold degradation after 75 hours of incubation. Pullulanase (4 U/mL) incubation resulted in scaffold degradation after 90 minutes. Combination degradation experiments resulted in hydrogel dissolution after 60 minutes (FIG. 6A).

Quantification of STMP Cross-Linking.

Figure 6:
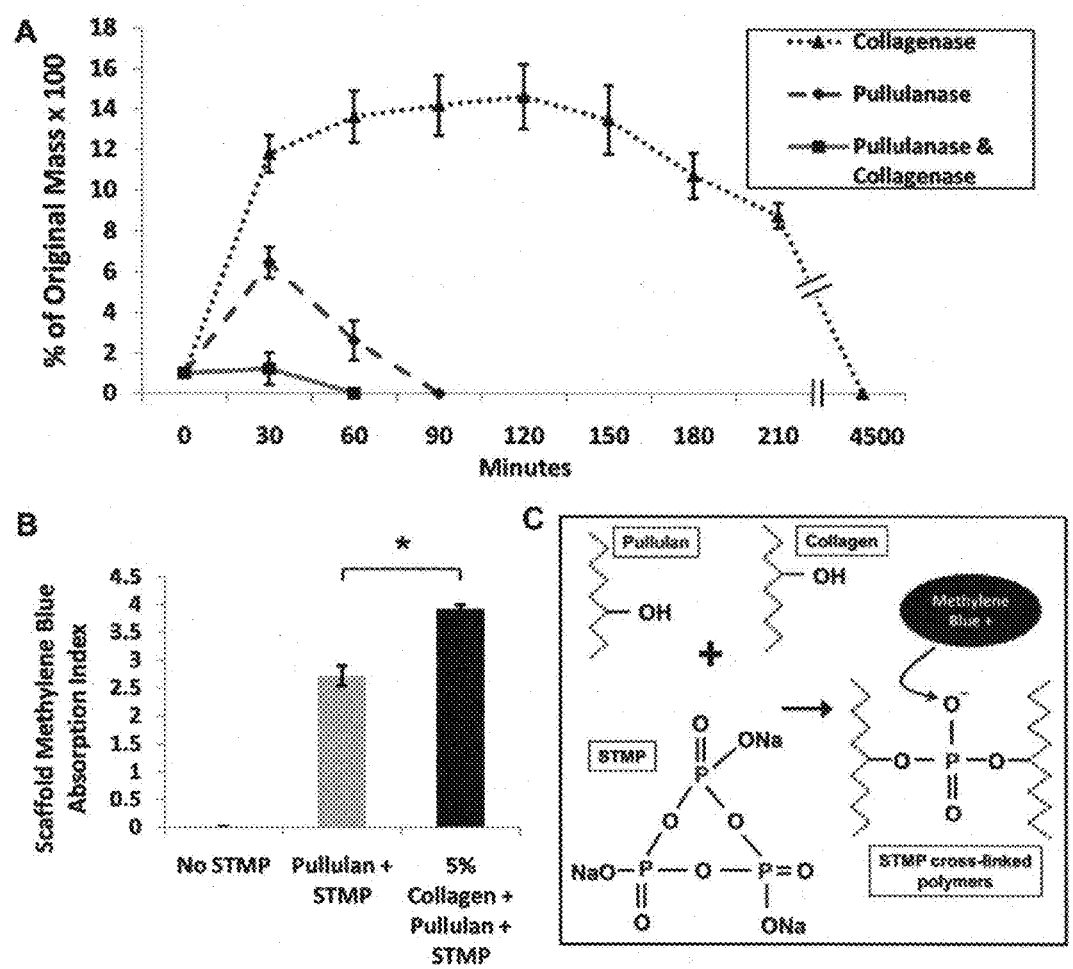
FIG. 6A-6C: 5% collagen-pullulan hydrogel degradation profiles and cross-linking quantification. Hydrogels were rapidly degraded in 60 minutes with combination pullulanase/collagenase A incubation (green line, square markers) and within 90 minutes after pullulanase only treatment (blue dashes, diamond markers) (A). Interestingly, collagenase A only treatment did not result in hydrogel degradation until over 75 hours later (red dots, triangle marker). This suggests that pullulan is the major stabilizing element of these hydrogels. N=6 for each condition. Based on methylene blue binding of STMP cross-links, we determined that both pullulan and collagen are cross-linked with STMP (B). Schematic of STMP cross-linking hydroxyl groups found on both pullulan and collagen (C). The anionic phosphate linkages are bound by cationic methylene blue dye (C).

Methylene blue absorption studies demonstrated that both pullulan and collagen are cross-linked by STMP (FIG. 6B). There is a significant increase in scaffold STMP absorption with the addition of 5% collagen to pullulan hydrogels (Scaffold $AI_{MB}$=2.7 for pullulan vs. 3.9 for pullulan with 5% collagen, p<0.01).

In Vitro Viability and Incorporation Assays.

Figure 7:
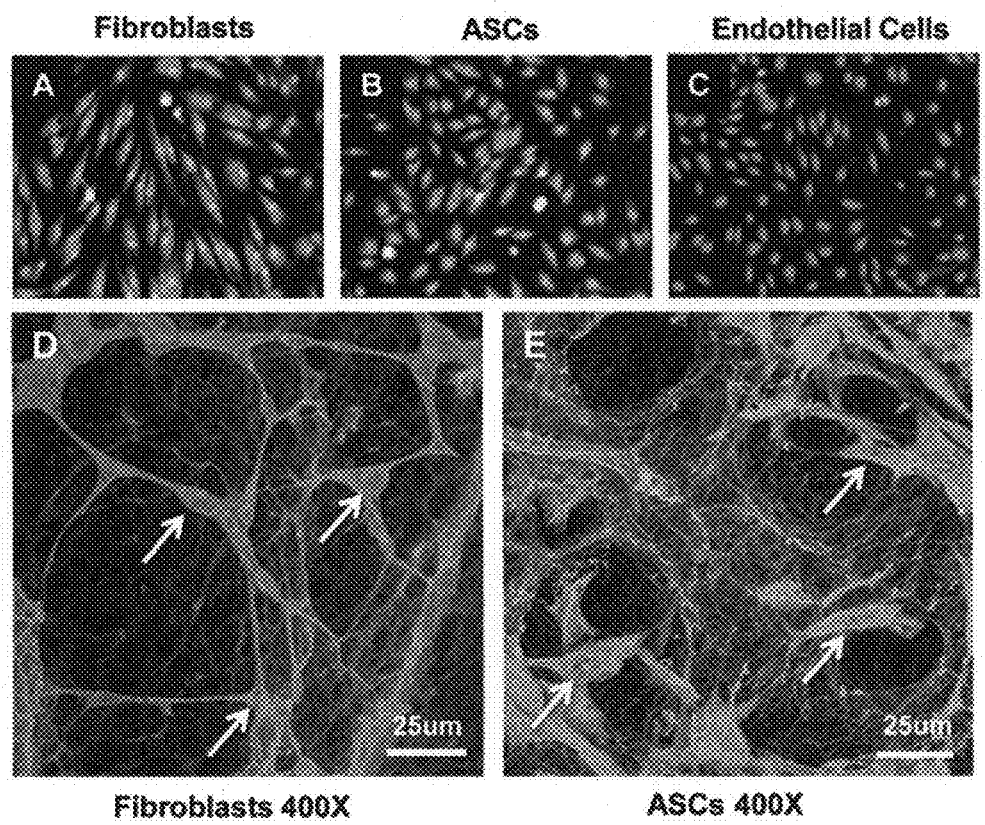
FIG. 7A-7E: In vitro cellular incorporation. Hydrogels were non-cytotoxic following incubation with fibroblasts, ASCs, and endothelial cells (A-C). Fibroblasts were viably incorporated into 5% collagen-pullulan hydrogels (arrows, D). Mesenchymal stem cells (arrows, E) attached and organized onto the scaffold in a sustainable manner. Additionally, the porous reticular network of the hydrogel scaffold is maintained in both images.

Fibroblasts, ASCs, and endothelial cells were viably sustained following 24 hour incubation with 5% collagen-pullulan hydrogels, exhibiting over 97% viability, similar to control populations seeded without hydrogels (FIG. 7A-C). Fibroblasts were successfully seeded with pullulan hydrogels and displayed invasion and attachment on SEM (FIG. 7D). ASCs were also well-organized within 5% collagen-pullulan hydrogel scaffolds on SEM (FIG. 7E).

Discussion

We have developed a novel method to fabricate porous collagen scaffolds within a pullulan-based hydrogel system. This technique is based on rapid desiccation of swollen hydrogels by phase inversion. We hypothesize that dehydration results in localized supersaturation and crystallization of KCl. Pullulan and collagen are forced to organize around the crystals in an interconnected network which results in reticular scaffold formation following KCl dissolution (FIG. 1G). Alternative techniques employed to induce scaffold porosity include emulsion freeze drying, solvent leaching, fiber bonding, high pressure supercritical fluid processing, gas foaming, self assembly molecules, and electrospinning. To our knowledge, this is the first demonstration of KCl crystallization-induced pore formation applied to fabricate collagen scaffold hydrogels.

Bioengineered collagen scaffolds with pore sizes of 50-300 μm have been reported. However, these data are from rigid non-hydrogel scaffolds that can tolerate greater pore sizes without collapsing. Hydrogels inherently have less stiffness and increased pore size generally results in collapse of gel microstructure. Given the inherent plasticity, permeability, and swelling properties of hydrogel materials, we hypothesized that 5% collagen hydrogels would be functional despite a smaller pore size compared to "hard" collagen scaffolds. Additionally, mathematical modeling of the 5% collagen hydrogel network showed that the porous ultrastructure best approximated that of unwounded normal murine dermis.

Hydrogels exhibit water retention attributes that make them an attractive biomaterial for cell and small molecule delivery. Their absorptive capacity and flexible nature have been utilized to remove exudative debris in various wound dressings. 5% collagen-pullulan hydrogels were incubated in both water and PBS and exhibited swelling ratios of approximately 10 to 30. This is consistent with published data on pullulan hydrogel hydration of greater than 90% and swelling ratios of elastin-based hydrogels ranging from 18 to 33. Incubation with water resulted in greater swelling compared to PBS, as expected due to increased osmotic swelling forces with hypotonic solutions. Increased swelling ratios at higher temperatures have also been seen with other hydrogels, attributed to disruption of secondary interactions and hydrogen bonds within polymers and facilitation of water absorption.

Pullulan alone in aqueous solution has been shown to be mostly viscous with a loss modulus greater than storage modulus over a wide range of concentrations. However, the cross-linking of pullulan by STMP results in elastic gel-like behavior, which has also been demonstrated in other studies. Rheologic data from our collagen-pullulan hydrogels show that with minimal porosity (no KCl), hydrogels behave more like an elastic solid gel. The addition of KCl, which we have shown acts as a porogen, augments hydrogel viscoelasticity. The improved scaffold porosity with KCl allows for greater fluid absorption, a higher water to polymer ratio, and more effective hydrogel behavior. Strain sweep testing demonstrated that the addition of 5% collagen increased the ability of hydrogels to resist deformation, perhaps by providing more substrate to be cross-linked and altering polymeric organization within the hydrogels.

5% collagen-pullulan hydrogels showed rapid dissolution in both pullulanase and pullulanase/collagenase solutions, but prolonged stability with collagenase only incubation, which suggests that pullulan plays the major role in structural stability. Methylene blue quantification of STMP cross-linking demonstrates that both pullulan and collagen are cross-linked by STMP, not surprising given that both polymers have free hydroxyl groups which can be linked by STMP (FIG. 6C). Scanning micrographs showed that the addition of collagen decreased pore size. It has been shown that collagen fibril formation is highly dependent on ionic interactions and pH, both of which are influenced by KCl crystallization. Increasing the collagen concentration may modulate KCl crystal formation and subsequent pore size. Polarizing light studies demonstrate that collagen is organized into fibrils, that different size fibrils are present, and that this matrix protein is found throughout the scaffold surrounding pores. Combining the SEM and polarizing light data, it can be deduced that cross-linked fibrillar collagen is arranged in a reticular network throughout the hydrogel scaffold.

The aqueous nature of hydrogel substrates provides an ideal environment for cellular growth and sustainability. For example, a pullulan-based hydrogel was shown to support vascular cell growth in culture, an injectable chitosan-based hydrogel permitted chondrocyte proliferation, and polyethylene glycol-based hydrogel scaffolds were shown to support human mesenchymal stem cell proliferation and differentiation. In vitro studies performed with our 5% collagen scaffold hydrogels showed high biocompatibility with fibroblasts, ASCs, and endothelial cells. In addition, fibroblasts and ASCs were well incorporated into these scaffolding constructs. These data demonstrate that collagen scaffold hydrogel delivery of wound repair and progenitor cells can potentially be used following dermal injury.

We have demonstrated that a pullulan-based collagen hydrogel can be fabricated with KCl-induced phase inversion and STMP cross-linking to form a reticular scaffold. This soft collagen scaffold displays excellent handling characteristics, durability, and a porous dermal-like ultrastructure that is maintained in vitro. Furthermore, cell types potentially involved in skin repair are viable sustained within these biomatrices. Although several hydrogel applications exist for wound dressings and hard collagen scaffolds such as bone and cartilage, options for hydrogel-based skin engineering continue to be limited. This biocompatible collagen scaffold promises to broaden hydrogel applications for skin engineering and can potentially be used to deliver organized matrix components, cells, and biomolecules for skin regeneration.

Example 2

Pullulan-collagen hydrogel scaffold provided MSCs with a protected three-dimensional environment within the wound bed. These scaffolds enabled improved cell engraftment in healing excisional wounds over current injection delivery methods. Engrafted MSCs contributed to improvements in healing and regeneration of normal tissue.

Figure 8:
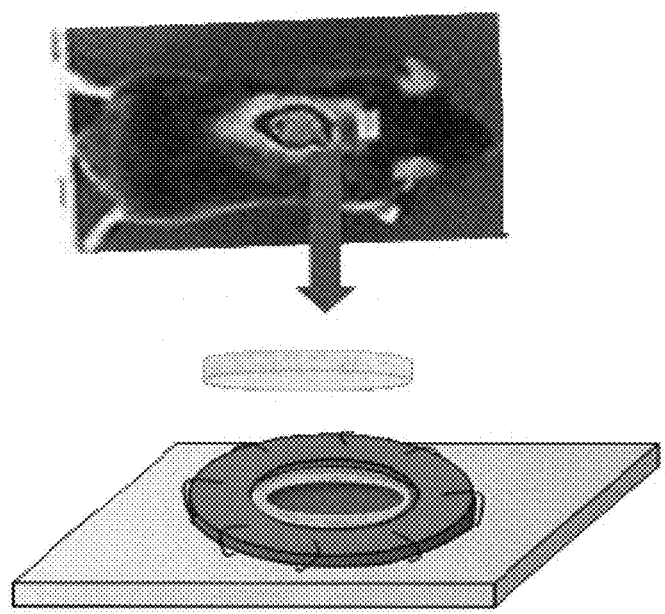
FIG. 8. Pullulan/collagen films were placed on the wound.

Pullulan/collagen films were placed on wound of the WT mice. The method is depicted in FIG. 8. Results: We found that the pullulan collagen applied wound healed much more effectively than the wound without the scaffold.

Figure 10:
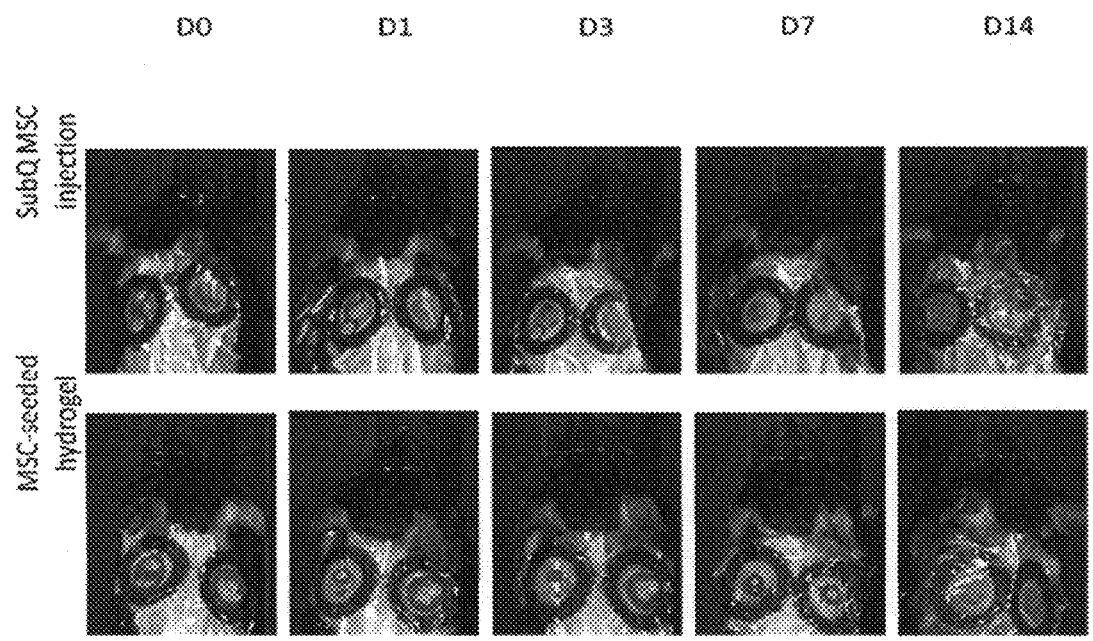
FIG. 10. Pullulan/collagen scaffold is seeded with MSCs survived longer period compared with subcutaneously injected stem cells.

Pullulan/collagen hydrogel were then seeded with mesenchymal stem cells (MSCs) on the wound (FIG. 10). The cells survivability was monitored by measuring at the luminescence.

Figure 9:
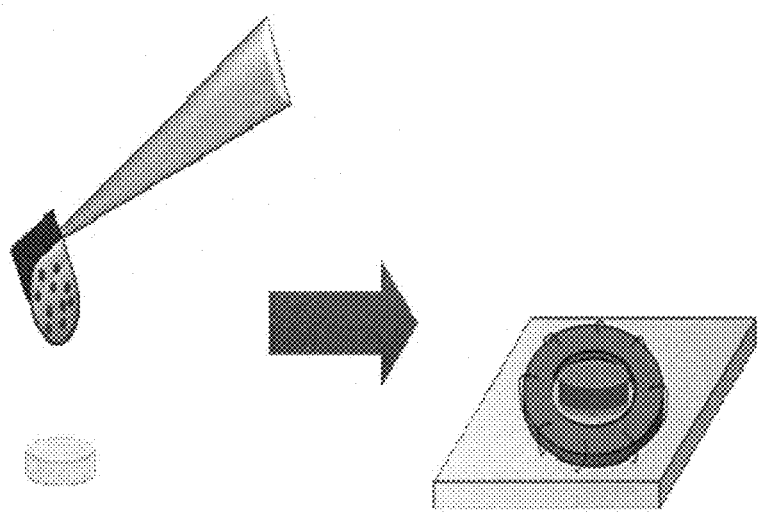
FIG. 9. Pullulan/collagen scaffold is seeded with MSCs and then applied on the wound.
Figure 11:
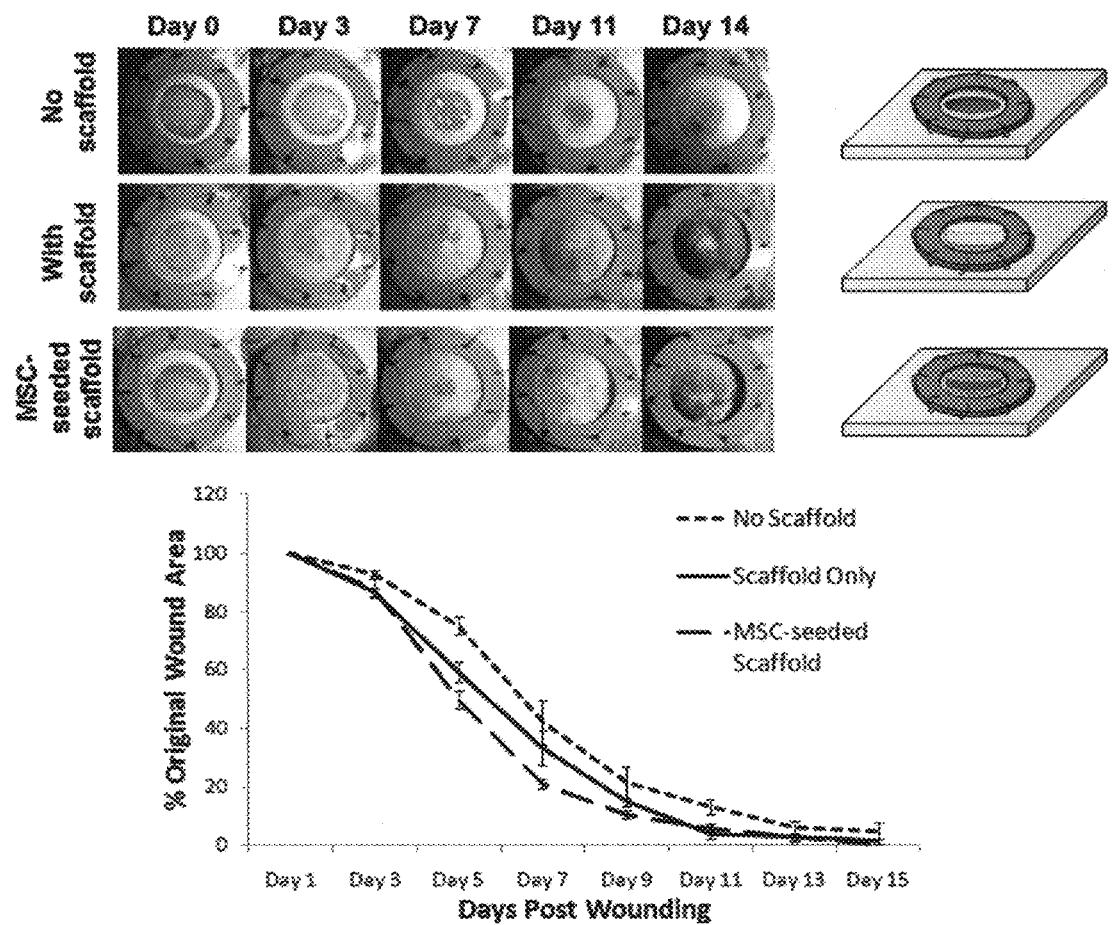
FIG. 11. Wounds that were treated with pullulan/collagen scaffold and seeded with MSCs healed faster than the unseeded and untreated wounds.
Figure 12:
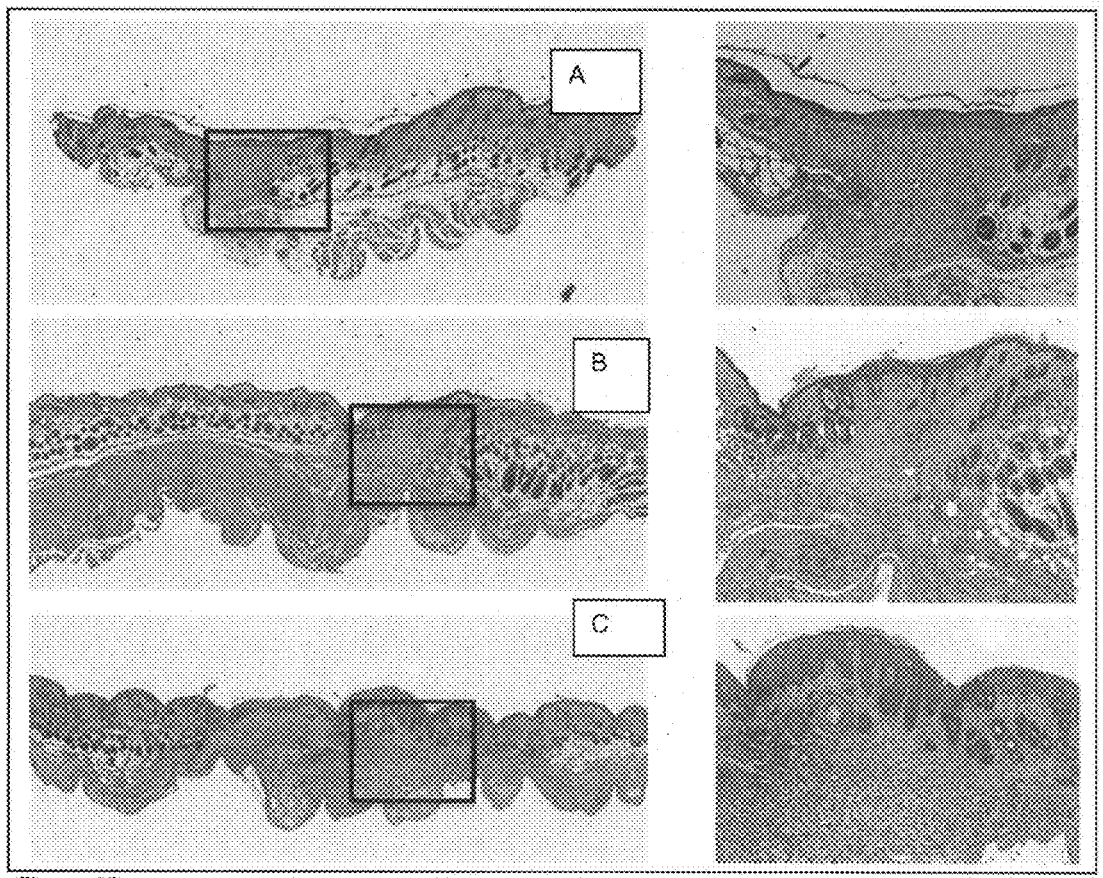
FIG. 12. Skin sections that were treated without scaffold (A), Pullulan/collagen scaffold alone (B), and scaffold seeded with MSCs (C). Note that the untreated wound healed with thick epidermis. The scaffold seeded with MSCs healed with normal epidermis with hair appendages.

We found the cells that were seeded with scaffold survived longer than those with subcutaneously injected MSCs. Furthermore, the wound treated with pullulan/collagen matrix healed much more effectively than the wound covered with nothing or matrix alone (FIGS. 9 and 11). We have also analyzed the quality of wound healing by histochemistry. We have noticed that the wounds treated with MSCs seeded cells healed with hair appendages. The untreated wounds healed with fibrotic epidermis.

What is claimed is:

1. A composition for wound healing comprising:
   a pullulan-collagen hydrogel film with controlled porosity which is cross-linked to form a reticular scaffold wherein pullulan and collagen are organized around salt crystals in an interconnected network such that the reticular scaffold is formed to define pores following salt dissolution and wherein said hydrogel comprises collagen at a concentration of from about 1 to about 12.5%; and
   regenerative cells within the pores.

2. The composition of claim 1, wherein the pores of from about 25 μm to about 50 μm in diameter.

3. The composition of claim 1, wherein scaffold porosity of said hydrogel ranges from about 50% to about 85%.

4. The composition of claim 1, wherein the regenerative cells are stem or progenitor cells.

5. The composition of claim 4, wherein the regenerative cells are mesenchymal stem cells.

6. The composition of claim 1, where the hydrogel further comprises regenerative growth factors.

7. The composition of claim 6, wherein the regenerative growth factors are printed on the hydrogel by micro-contact printing.

8. The composition of claim 6, wherein the regenerative growth factors include a vascular endothelial growth factor (VEGF).

9. The composition of claim 1, wherein the hydrogel further comprises an antimicrobial agent.

10. The composition of claim 1, further comprising a dressing suitable for wound repair.

11. The composition of claim 10, wherein the dressing comprises a breathable protective layer.

12. A composition for wound healing comprising:
    a pullulan-collagen hydrogel film with controlled porosity which is cross-linked to form a reticular scaffold wherein pullulan and collagen are organized around salt crystals in an interconnected network such that the reticular scaffold is formed to define pores following salt dissolution and wherein said hydrogel comprises collagen at a concentration of from about 2.5 to about 10%; and
    regenerative cells within the pores.

13. The composition of claim 12, wherein the pores of from about 25 μm to about 50 μm in diameter.

14. The composition of claim 12, wherein scaffold porosity of said hydrogel ranges from about 50% to about 85%.

15. The composition of claim 12, wherein the regenerative cells are stem or progenitor cells.

16. The composition of claim 15, wherein the regenerative cells are mesenchymal stem cells.

17. The composition of claim 12, where the hydrogel further comprises regenerative growth factors.

18. The composition of claim 17, wherein the regenerative growth factors are printed on the hydrogel by micro-contact printing.

19. The composition of claim 17, wherein the regenerative growth factors include a vascular endothelial growth factor (VEGF).

20. The composition of claim 12, wherein the hydrogel further comprises an antimicrobial agent.

21. The composition of claim 12, further comprising a dressing suitable for wound repair.

22. The composition of claim 21, wherein the dressing comprises a breathable protective layer.

* * * * *